(12) United States Patent
Souissi

(10) Patent No.: US 11,291,386 B2
(45) Date of Patent: Apr. 5, 2022

(54) SYSTEM AND METHOD FOR LIVE PATIENT TRACKING FOR SURGICAL CENTERS AND HOSPITALS

(71) Applicant: Slim Souissi, San Diego, CA (US)

(72) Inventor: Slim Souissi, San Diego, CA (US)

(73) Assignee: Ospeitek, Inc., San Diego, CA (US)

( * ) Notice: Subject to any disclaimer, the term of this patent is extended or adjusted under 35 U.S.C. 154(b) by 0 days.

(21) Appl. No.: 16/897,835

(22) Filed: Jun. 10, 2020

(65) Prior Publication Data
US 2021/0386326 A1    Dec. 16, 2021

(51) Int. Cl.
*A61B 5/11* (2006.01)
*A61B 5/00* (2006.01)

(52) U.S. Cl.
CPC .......... *A61B 5/1113* (2013.01); *A61B 5/002* (2013.01); *A61B 5/742* (2013.01)

(58) Field of Classification Search
CPC ........ G16H 40/20; G16H 40/60; G16H 40/63; G16H 40/00; A61B 5/00; A61B 5/0022; A61B 5/1112; A61B 5/1113; A61B 5/1115; G06F 19/00; G08B 21/02; G08B 21/04; G08B 21/0446; G08B 21/18; G08B 21/182
See application file for complete search history.

(56) References Cited

U.S. PATENT DOCUMENTS

| 2008/0048826 A1* | 2/2008 | Agrawal | G16H 40/20 340/5.61 |
| 2011/0001605 A1* | 1/2011 | Kiani | G16H 30/20 340/5.6 |
| 2020/0113435 A1* | 4/2020 | Muhsin | G16H 40/63 |

OTHER PUBLICATIONS

NPL_search.pdf (Aug. 13, 2021).*

* cited by examiner

*Primary Examiner* — Van T Trieu
(74) *Attorney, Agent, or Firm* — Pablo Meles

(57) ABSTRACT

A method for live patient tracking for surgical centers and hospitals is provided comprising tracking patient journey through a healthcare facility. The method also comprises overlying tracked journey data on patient surgical status data and visualizing the overlaid journey data and surgical status data on a display. Visualization of data is performed on the display of a TV screen, a tablet, a desktop computer, a tablet or a smartphone. The visualized data includes patient indoor location within the healthcare facility. Patient indoor location is performed by means of an indoor positioning system such as Real Time Location Service (RTLS) system.

22 Claims, 11 Drawing Sheets

SYSTEM AND METHOD FOR LIVE PATIENT TRACKING FOR SURGICAL CENTERS AND HOSPITALS

FIELD OF THE INVENTION

The present disclosure is in the field of hospital and surgical management. More particularly, the present disclosure provides systems and methods of tracking a patient movement through the full surgical process and selectively publishing related information for use by medical staff and viewing by family.

BACKGROUND

Patient movement within a hospital or surgical center generally follows a standard process as a patient moves between different locations within a facility. As illustrated by FIG. 3, for example, in a simple patient journey, a patient moves from waiting room (301) to pre-op room (302) to operating room (303a) to recovery room (304). In some cases, patients could move to radiology rooms to take an x-ray or a scan or to special rooms to perform physical examination, lab testing or other types of medical services.

In some hospitals, it is common to find hospital staff attempting to locate a patient inside the facility. This may occur several times between patient admittance and discharge.

A family member may request information about a patient at a hospital front desk or when they call a hospital operator. The operator may have to make multiple calls to determine patient location. The operator may have to call pre-op nursing station, operating room (OR) nursing station, recovery nursing station and/or radiology department.

The operator may not get a response to their calls because medical staff is busy. The operator may have to dispatch personnel to walk through the facility to find out about patient status. This causes disruptions and delays at the front desk and operator function and creates inefficiencies in managing the hospital or other facility. Medical staff may also need to know the location of a patient either to meet a patient, or to be ready for a patient.

In addition to location, medical staff usually needs to know patient status. A patient in pre-op may be ready to be moved to operating room. A patient may have been examined by a nurse and is ready to be seen by a physician. A patient may be inside an operating room but the physician is unaware and is instead talking to another patient in a preOp area, a PACU area or even making notes about a prior surgery. In each of these examples, the patient's status is not known by those who need to know it.

To learn location and status of a patient, departments frequently call each other. This may be a time-consuming process, especially when multiple calls must be made. Receiving and responding to these phone calls to find patient location/status is also an interruption to nursing stations that sometimes cannot answer calls because they are occupied with tasks on their unit.

Some medical facilities track patients inside their facility using RTLS (Real Time Location Services) tracking technology. Centrak uses RTLS to track medical staff members.

Some medical facilities have installed systems for staff to enter location changes as they occur. This enables such facilities to minimize phone calls to find a patient location. But those system are cumbersome and may require going through many layers of menus to update status. Software provided by Epic Systems Corporation uses manual tracking and status updates of patients.

Manual entry of location is inefficient, error prone and not live. Inefficiency stems from the fact that medical staff has to enter/log location change multiple times for each patient. Such systems are error prone because medical staff is often too busy providing medical care and they may forget to log location change to the system. Whenever medical staff forgets to manually change the location, monitors and displays will show wrong patient location, potentially creating confusion and delay.

SUMMARY

Surgical centers and hospitals need solutions that simplify patient location determination and patient status communication. Systems and methods described herein provide a comprehensive solution solving the following problems.

a. Tracking and visualizing patient location inside the medical facility b. Making patient location information available to medical staff in real time via monitors or other displays as applicable.

c. Using patient location data to keep patient family informed of patient journey and progress through various stages, reducing inquiries related to patient status and improving customer satisfaction.

d. Enabling staff to mark changes to patient status when and where it happens and making that data available to medical staff in real time. A pre-op nurse may mark a patient as ready to be moved to an operating room. Staff in charge of moving the patient to the operating room receive and use this information without having to make calls.

e. Notifying medical staff about events relevant to their workflow in real time.

d. Notifying family members about the status of the patient.

DETAILED DESCRIPTION

Systems and methods described here provide an approach that eliminates inefficiencies in locating a patient and avoids or simplifies any manual effort in keeping location up to date. Systems and methods further reduce errors in location by not relying on medical staff finding time to update systems during their schedule and automatically use location information for meaningful actions such as keeping family members informed or keeping medical staff updated automatically, continuously and in real time.

Bluetooth Low Energy (BLE) beacon technology is used for patient tracking in medical facilities, such as surgical centers, hospitals and nursing homes. A BLE beacon is attached to the patient wristband, medical chart or gown to track patient location. A preferred location to attach the BLE beacon is on the patient wristband.

BLE receivers are installed at various places inside the facility to listen to beacon transmits. These BLE receivers relay received beacons and their signal strength to cloud servers. Cloud servers use inputs from some or all BLE receivers inside a facility to determine the location of a particular BLE beacon and hence the patient.

BLE receivers in conjunction with cloud servers use existing indoor positioning technologies such as angle of arrival information, signal strength or triangulation to locate a beacon. Each beacon is uniquely paired with a single patient therefore finding the position of a beacon means finding the position of the patient paired with that beacon.

The system updates internal monitors and displays with patient location and status information relevant to medical staff. The system updates waiting room monitors and displays with patient status relevant to family members.

The system sends automatic SMS messages to family members depending on progress in patient journey. The system allows settings and configurations to specify conditions/trigger points for these automated messages. For example, a surgical center could configure the system to send automated messages to family members when surgery finishes and the patient has been moved to recovery room. Text messages can also be automatically sent when patient enters the operating room or is ready to see family members.

The system uses display input tablets (or touch screen TVs) where the list of patients shown is based on patient location. For example, tablets in pre-op nursing station show just the patient list in pre-op and a nurse could update status of that patient in just one-click.

Figure 1:
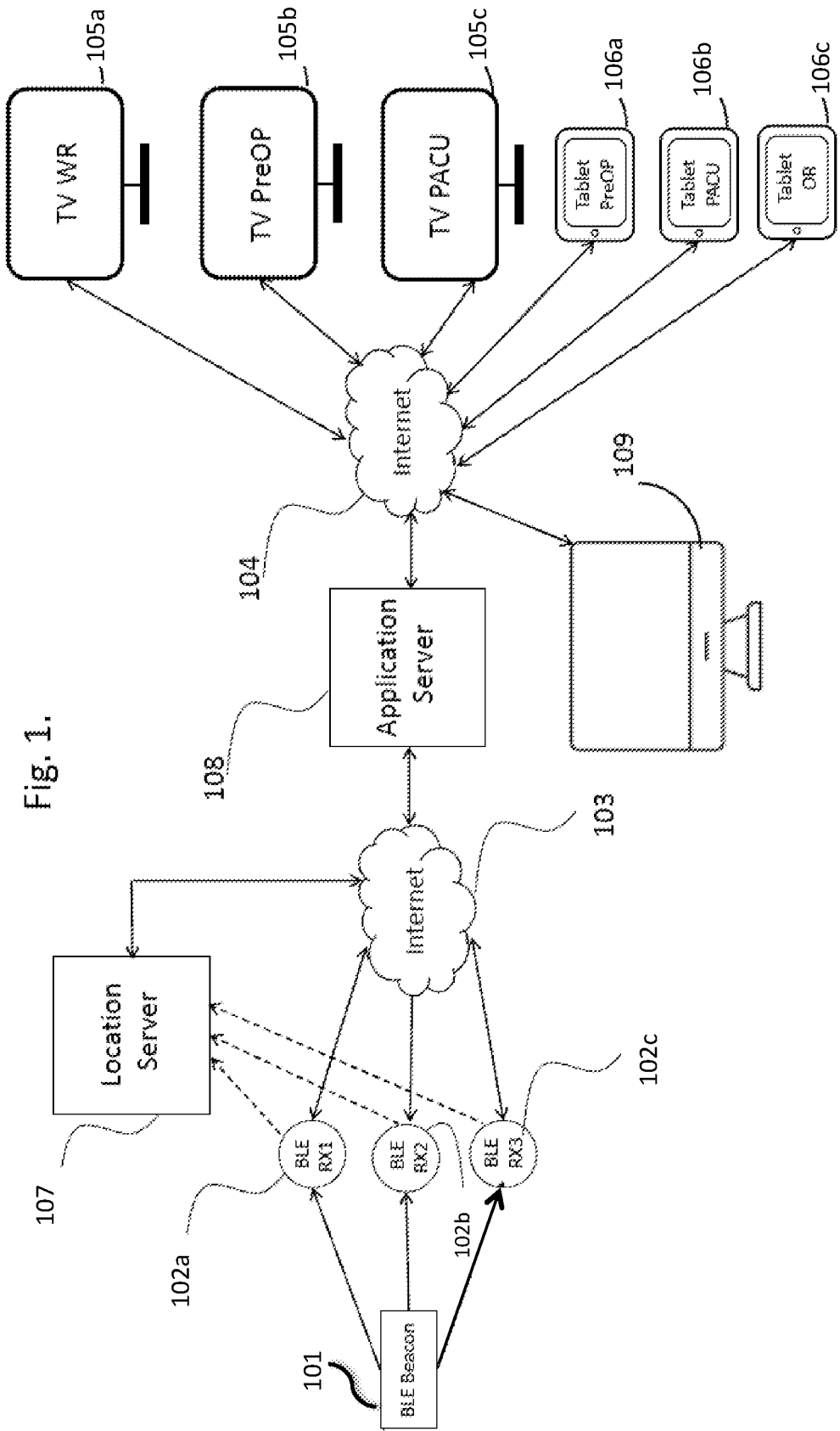
FIG. 1 is a block diagram of a system for live packing of patients in a hospital or surgical center according to an embodiment of the present disclosure.

Turning to the figures, FIG. 1 illustrates a high-level view of an entire patient management system provided herein. The system consists of at least one BLE beacon (101) attached to a patient wristband. BLE receiver cells (102a, 102b and 102c) are affixed at various locations inside the medical facility. The system further comprises a location determination server (107) and TV monitors/displays (105a, 105b and 105c) at various locations inside the medical facility as well as tablets (106a, 106b and 106c) installed throughout the facility and desktop (109) set up in the front desk.

BLE receiver cells 102a-b are affixed at various locations such that there is reliable coverage for locations where the patient may be. For the system to continue working even if a receiver (102a, 102b and 102c) is disconnected, redundant cells (102a, 102b and 102c) are provided at areas of the patient journey. BLE receivers (102a, 102b and 102c) collect beacon identification signals from beacons 101 in the vicinity and send this information to location server (107) along with the beacon MAC address and the signal strength at which the signal was received.

This information is sent over the public internet or private network over secure and private channels. The location server (107) calculates the beacon position and sends it to an application server (108). The application server (108) communicates to TV screens as well as tablets and computers within the facility and outside the facility. According to a preferred embodiment of the present invention, TV screen (105a) is installed at the surgical center waiting room (WR) and visualizes the patient location and status so patient family and others may learn of patient status by viewing the TV screen (105a) within the waiting room or elsewhere.

Figure 2:
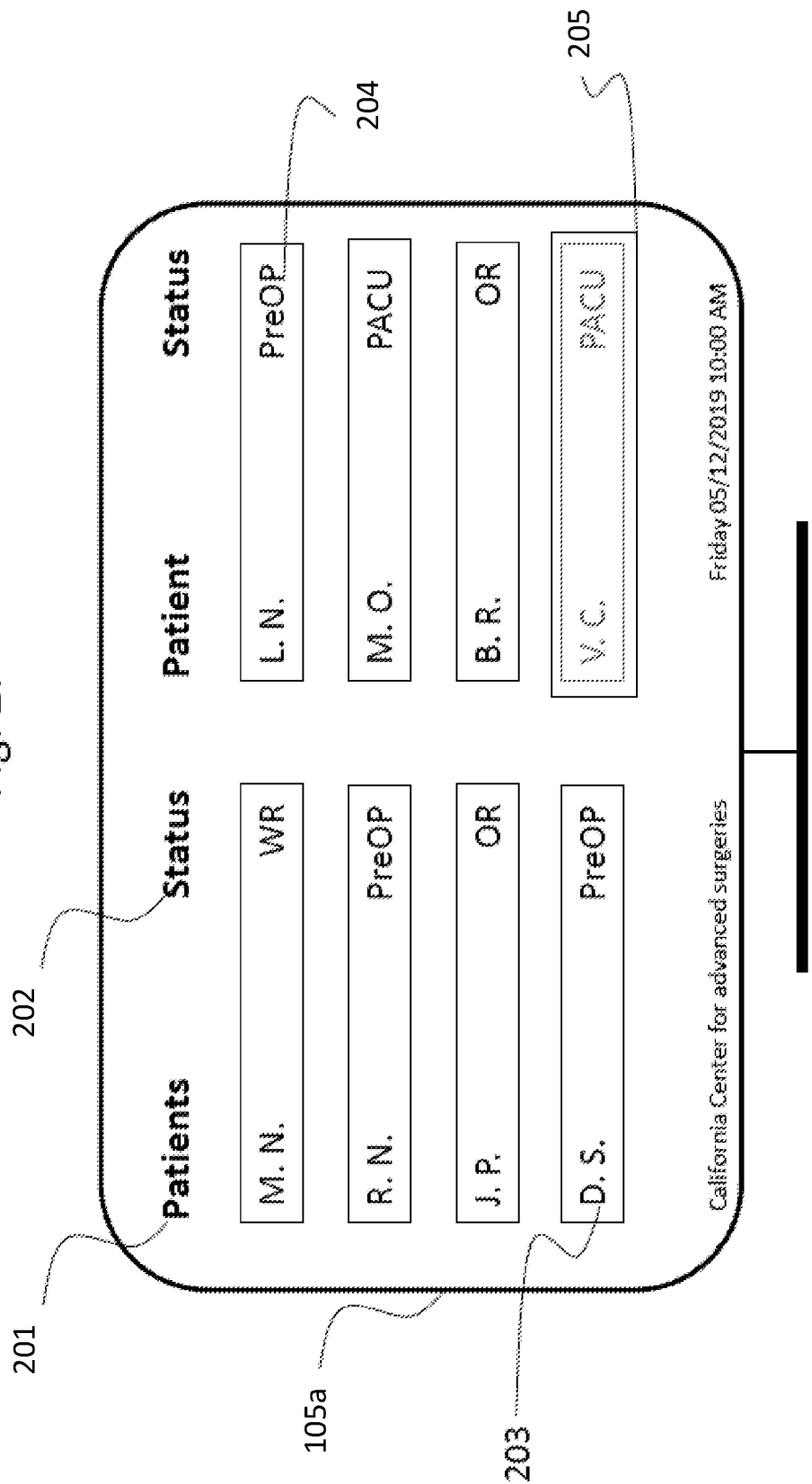
FIG. 2 is a rendering of the waiting room TV screen displaying a list of patients inside a surgical center along with their status according to an embodiment of the present disclosure.

FIG. 2 illustrates a rendering of the waiting room TV screen (105a). The screen displays a list of patients (201) inside the surgical center along with their status (202). Patients names are displayed while meeting HIPPA (Health Insurance Portability and Accountability Act) rules and regulations. In this example, only patient initials (203) are shown. Alternatively, an alphanumeric code may be used as a unique identifier for the patient.

The status of patient (204) is shown in front of the initials. The patient location within the facility is derived from the information sent by location server (107) to application server (108). When a patient is in the Post-Anesthesia Care Unit (PACU) and the patient is ready to meet with family, a PACU nurse uses tablet (106b) in the PACU area to signal to the waiting room TV (105a) that the patient is awake and able to meet family.

Figure 4:
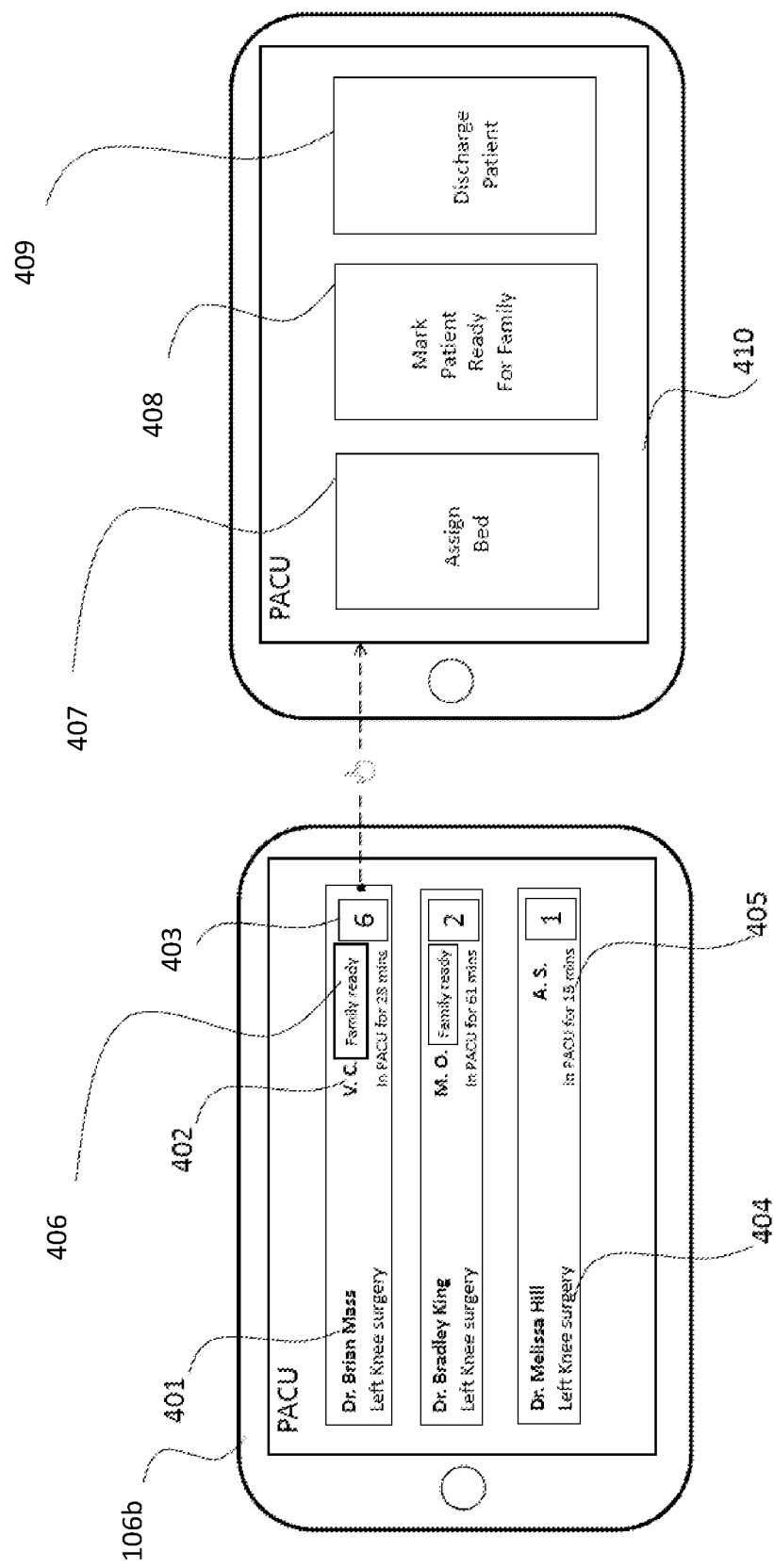
FIG. 4 illustrates actions resulting when a PACU nurse selects patient initials on a PACU display according to an embodiment of the present disclosure.

As illustrated in FIG. 4, when the PACU nurse clicks on patient initials (402), screen (410) appears. By selecting button (408), the nurse can signal patient status on the waiting room TV. The entire row (205) of the waiting room TV with the patient initials and status changes color to green to signal to the family that the patient is ready to meet and that they need to talk to the front desk to be escorted to the PACU area.

Front desk personnel respond to the signal from the PACU nurse by selecting on "family ready" button (406) from their desktop computer (109) to signal to the PACU nurse that the family is moving to PACU area to meet the patient. Label (406) shows up on tablet (106b) to message to the PACU nurse that the patient family is in front of the PACU entrance or is ready to be picked up from the waiting room. At the same time label (811) illustrated in FIG. 8 appears on TV screens (105b) and (105c) to signal family readiness to see the patient.

The signaling and visualization scheme provided herein may save the front desk and the PACU nurses time. Personnel need not keep calling each other or walking back and forth between the waiting room and the PACU area to check on patient status and communicate patient information to family and others.

Figure 3:
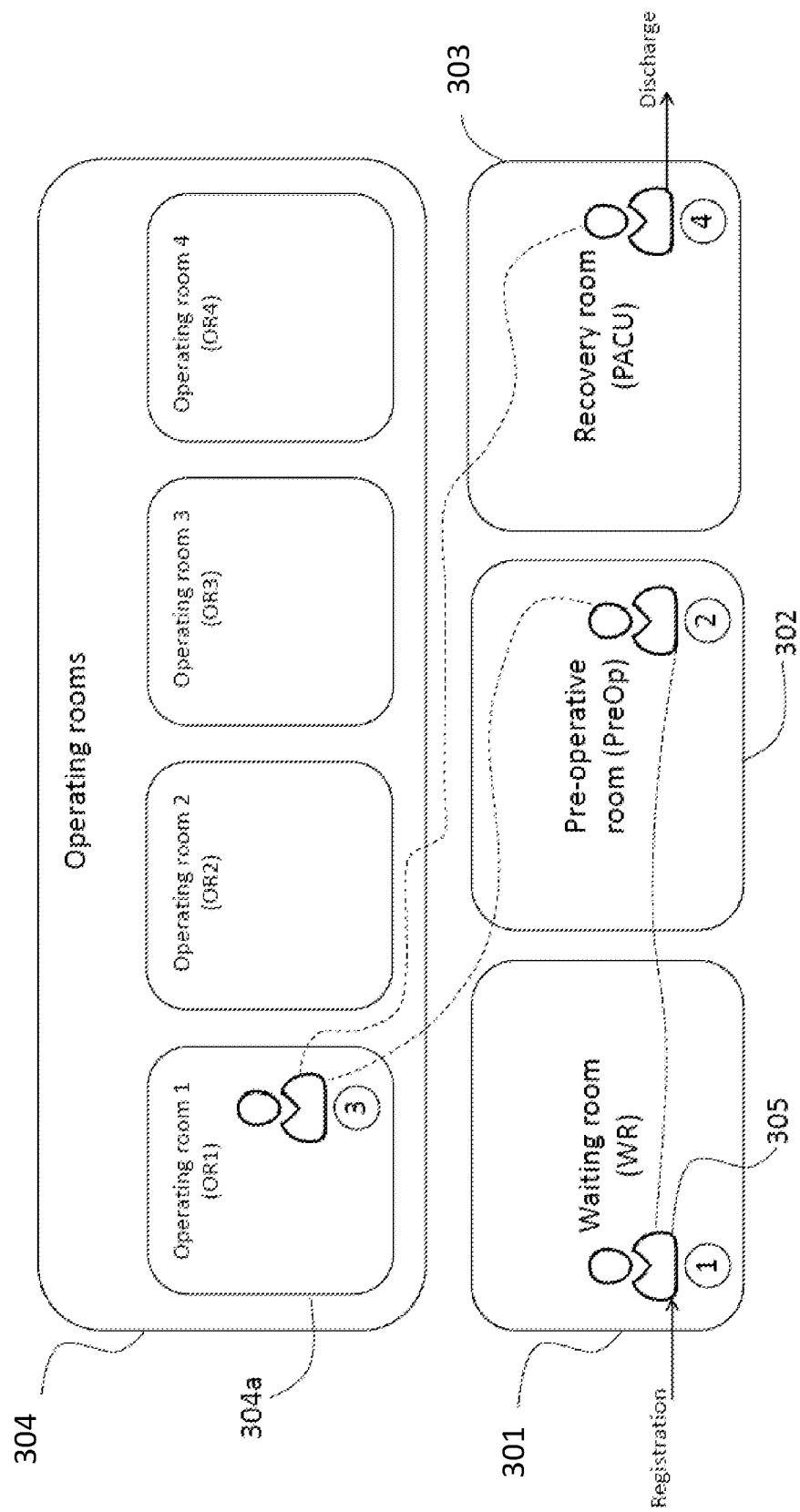
FIG. 3 illustrates a journey of a patient from registration at waiting room to surgery preparation at pre-operative room according to an embodiment of the present disclosure.

FIG. 3 illustrates the journey of patient (305) from (1) registration at waiting room (301) to (2) surgery preparation at pre-operative room (302). The patient continues to (3) surgery at operating room (304a) and to PACU room (303) for recovery and discharge.

FIG. 4 illustrates shows a user interface for a typical tablet (106b) deployed in PACU (303). Patients within the PACU area may be listed in the chronological order of their arrival at the PACU area. Displayed information includes the physician name (401), type of procedure (404), time spent in PACU (405), bed assigned to patient (403), and patient initials (402). To comply with HIPPA and convey information to staff members regarding patient identity, the system may display the patient identifier as full name, initials, first name only or an alphanumeric code.

Staff may choose how best to display patient information based on the location of the tablet or TV screen within the facility or based on other factor(s). When the PACU nurse selects a patient identifier, he/she is shown screen (410). The nurse is given options to assign a bed to the patient using button (407), to mark the patient as completed recovery and ready to meet family, or to discharge the patient with button (409). When the PACU nurse selects button (408), the patient name (205) on TV screen (105*a*) in the waiting room turns green.

Front desk personnel may respond by selecting "family ready" button (901) from desktop computer (109) to signal the readiness of the family to meet the patient in PACU. This causes indicator "family ready" (406) to show up on the tablet informing the PACU nurse that the patient is available in the waiting area or elsewhere. Indicator (811) on the PACU TV (105*c*) and PreOp TV (105*b*) may also appear to signal the readiness status of the waiting family.

Figure 5:
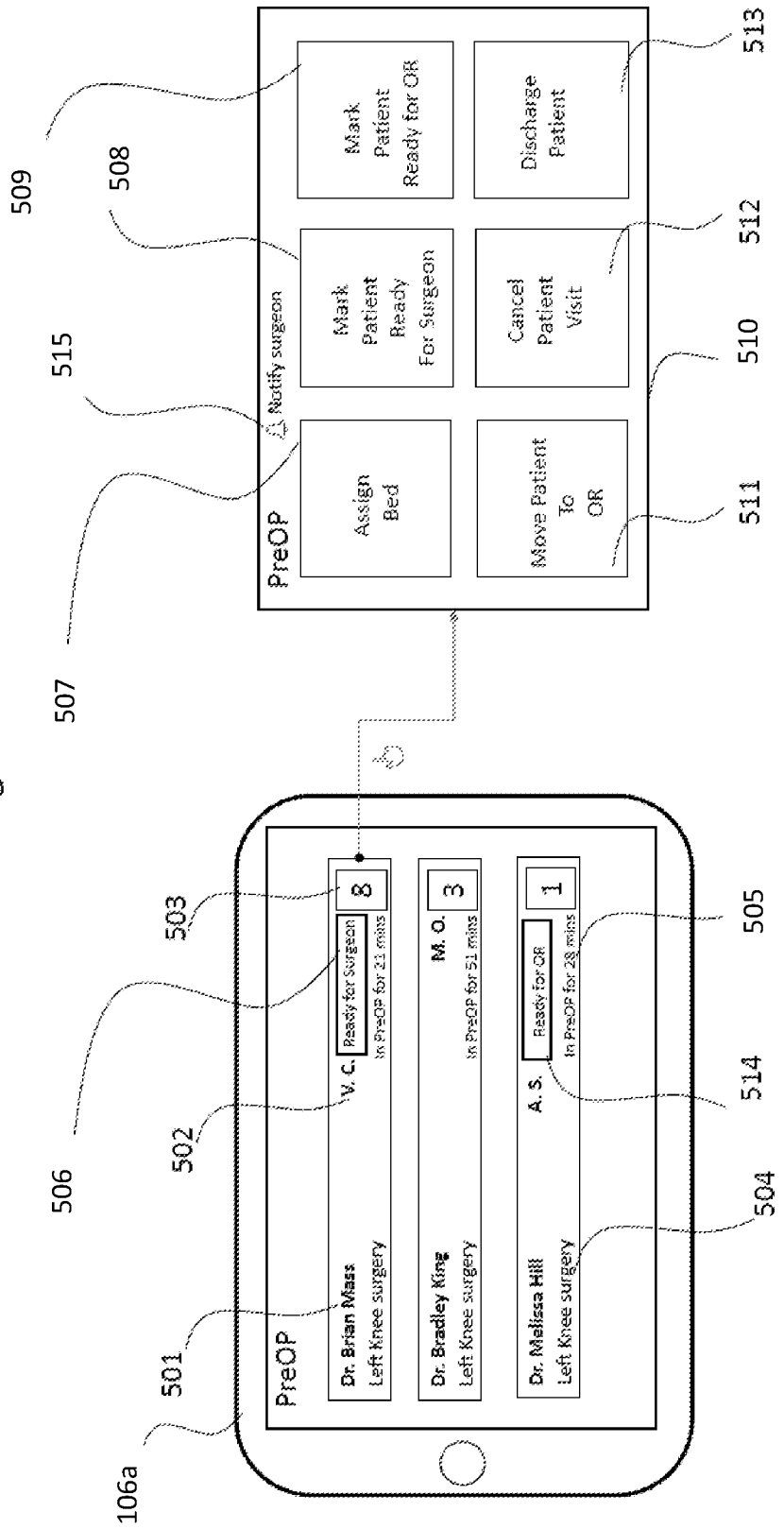
FIG. 5 illustrates a user interface for a typical tablet deployed in a pre-operative area according to an embodiment of the present disclosure.

FIG. 5 illustrates a user interface for a typical tablet (106*a*) deployed in the pre-operative area (302). Patients in the pre-operative area (302) may be listed in chronological order of their arrival. Displayed information includes the physician name (501), type of procedure (504), time spent in PreOp (505), bed assigned to patient (503), and patient initials (502). When the PreOp nurse selects a patient identifier, she/he is shown screen (510). The nurse is given the options to assign a bed to the patient using button (507) or button (508) to mark the patient as ready to see physician for OR consultation and interview. This action causes indicator (506) to appear on the tablet and indicators (813) to appear on TV screens (105*b*) and (105*c*).

FIG. 5 also exhibits button (515) that allows for a one-click notification via text messaging to the physician about the patient readiness for consultation in the PreOp area. Once the patient is approved by the physician to have surgery, the nurse selects button (509) to signal patient readiness to move to the operating room (OR) for surgery. This action causes indicator (514) to appear on the tablet and indicator (812) to appear on TV screens (105*b*) and (105*c*).

Figure 6:
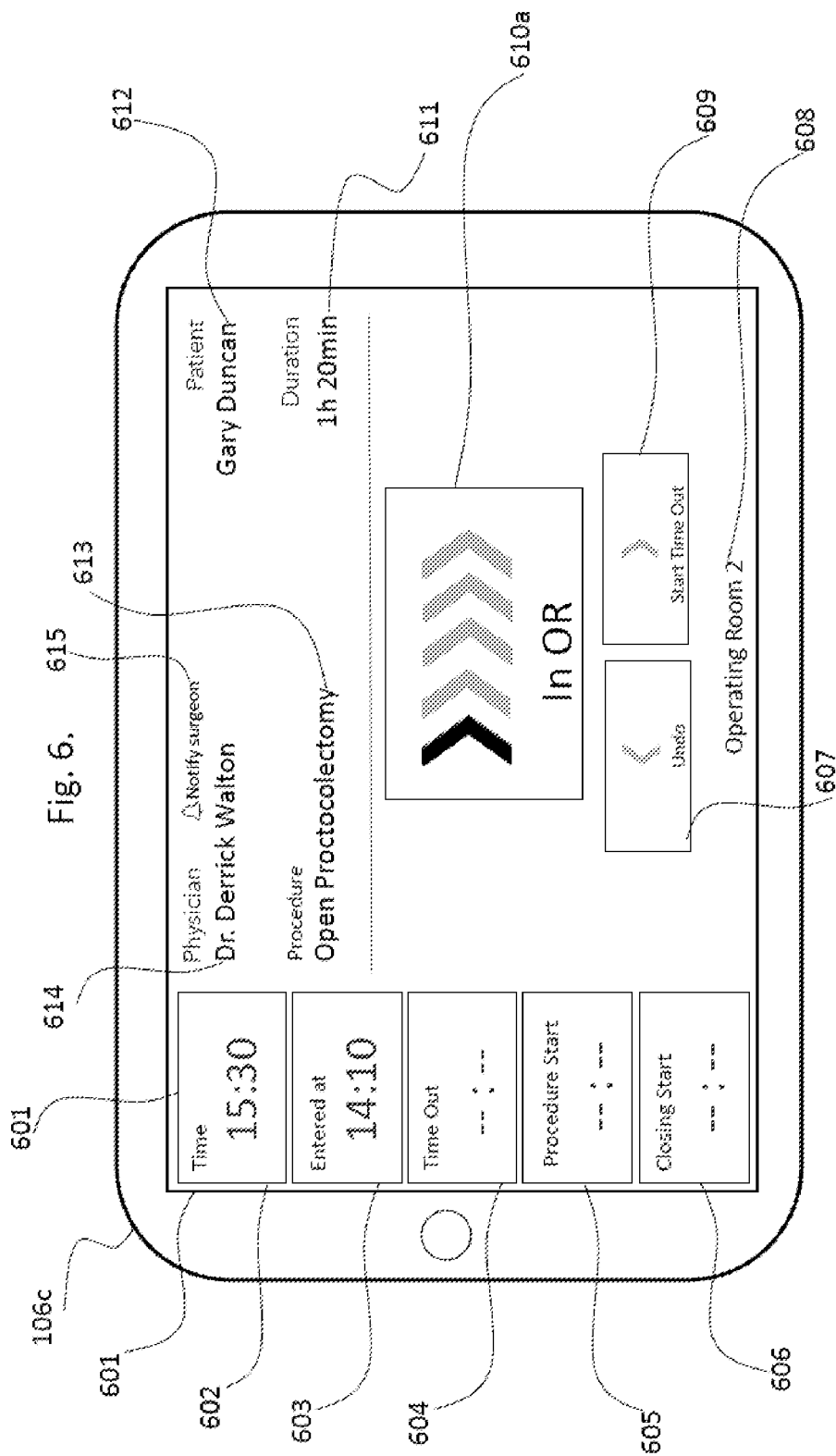
FIG. 6 depicts a sample user interface for tablet placed in the operating room according to an embodiment of the present disclosure.

FIG. 6 depicts a sample user interface for tablet (106*c*) that is placed in the operating room. When the patient is detected in the OR, tablet (106*c*) changes from a screen showing icon "waiting for patient" to the user interface illustrated by FIG. 6. The physician name (614) is shown along with a notification bell (615) to allow for notifying the physician manually of the readiness of the patient for surgery.

Alternatively, when the patient enters the operating room, a text message is sent to the physician notifying the physician of patient readiness. Indicator (814) is simultaneously displayed on screens (105*a*) and (105*b*) so personnel involved with the subject surgery are updated about the event "patient entrance to the OR". The tablet also shows the patient name (612) in full format, as initials, or as a unique alphanumeric identifier based on system settings. The interface also shows procedure type (613) and the duration of surgery (611) measured from the time the patient entered the operating room.

Actual time (602) is read from the application server (108) and used across the screens deployed within the surgical center as a synchronous common clock for the center. Block (603) represents the time at which the patient entered the operating room.

As surgery continues, the nurse selects button (609) to signal the start of the "Time Out" event. This event represents a recapitulation and reassurance of accurate patient identity, surgical site, and planned procedure. The status of block (610*a*) changes to show state (610*b*). Simultaneously, the state for block (808) depicted in FIG. 8 displayed on screens (105*b*) and (105*c*) changes to reflect the new status. Blocks (610*a*) on tablet (106*c*) and (808) on TV screens (105*b*) and (105*c*) remain synchronized and show the same state as surgery progresses. The nurse may select button (609) a second time to signal the start of the procedure.

Figure 7:
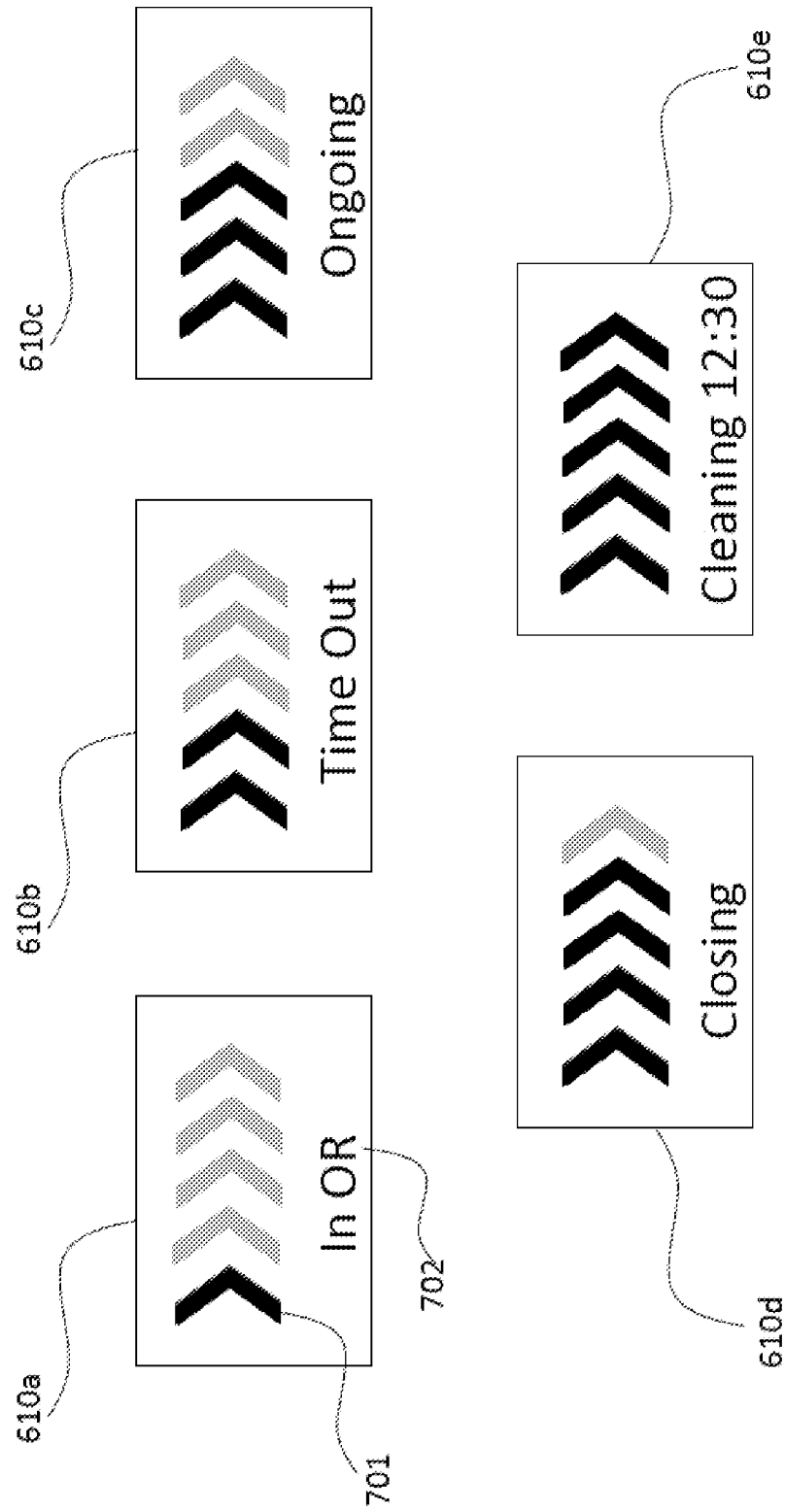
FIG. 7 is a depiction of designations of patient status during and after surgery according to an embodiment of the present disclosure.

Items labeled (610*b-e*) are depicted in FIG. 7. The status of block (610*a*) changes to show "ongoing" state (610*c*) indicating that the surgery is in progress. After the surgery is completed and "closing" starts, the nurse selects button (609) a third time to signal the start of "closing". The status of block (610*a*) changes to show closing state (610*d*).

The patient's departure from the operating room is detected through the tracking system. Location server (107) signals the new patient position to application server (108). Block (610*a*) changes to state (610*e*) signaling that "room cleaning" event has started. A timer is displayed on the tablet (106*c*) to estimate turnover time of operating room. The cleaning crew stops the timer as soon as the room is cleaned and ready to receive the next patient. The estimated turnover time is stored in the application server (108) for subsequent evaluation and analysis.

Figure 8:
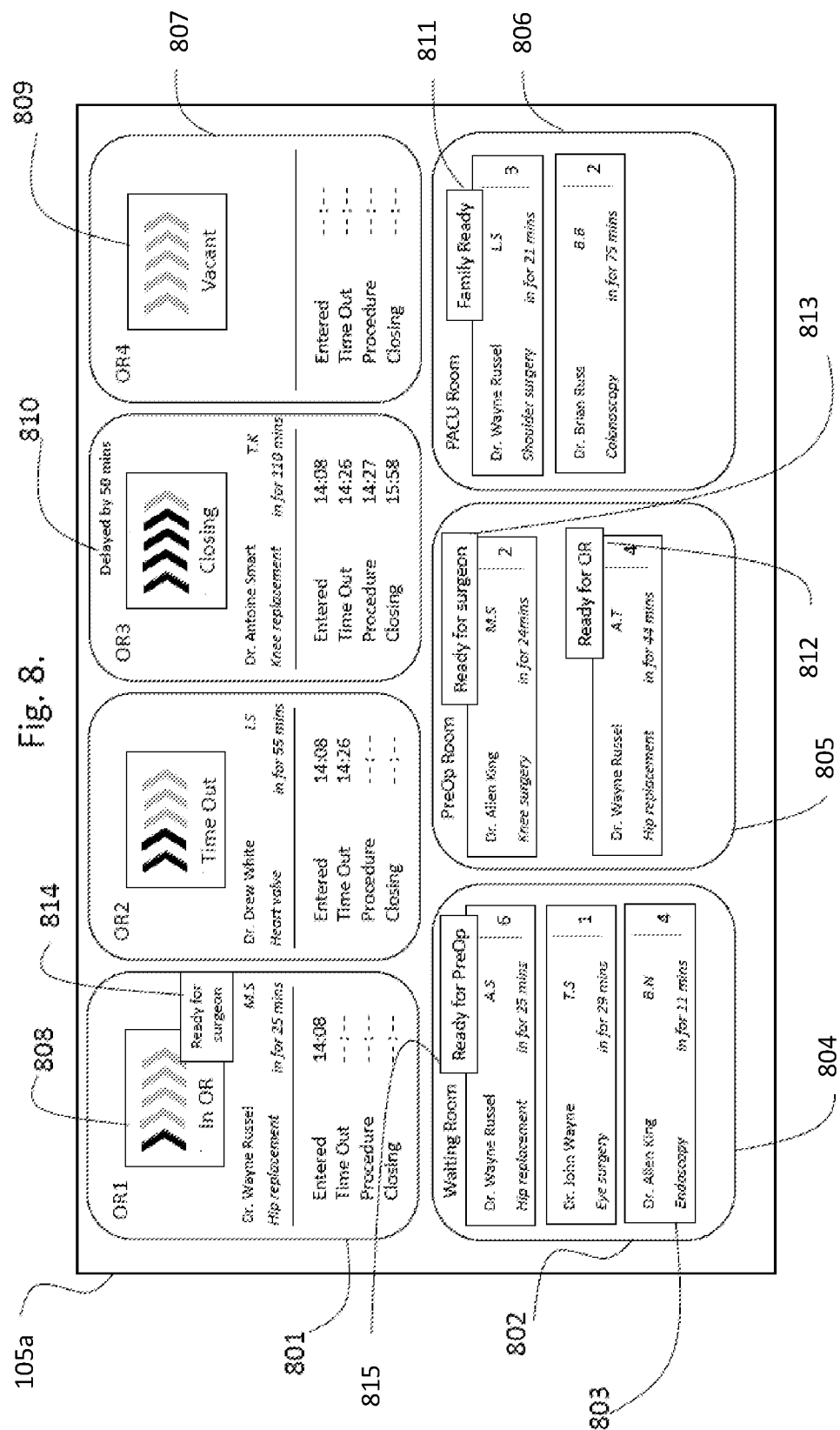
FIG. 8 illustrates an interface displayed on TV screens placed in a PreOp area and TV screens placed in a PACU area according to an embodiment of the present disclosure.

FIG. 8 illustrates an interface displayed on TV screen (105*a*) placed in the PreOp area and screens 105(*b*) placed in the PACU area. Screens (105*a-b*) typically display the same interface at all times. Block 801 represents the operating room quadrant. The status of the surgery is shown by progress arrows (808). Statuses include "in OR" when patient enters OR, Time Out, Procedure Start and Closing. When the room is vacant it is illustrated by image (809). Inside quadrant (801) the system displays patient initials, doctor name, procedure type and time spent inside the OR.

The system also keeps a record of procedure events since the patient enters the room. This gives a detailed view of the status of the operating rooms within the surgical center and helps staff members to plan their activities based on patient status visualized live on screens (105*a*) and (105*b*). For example, nurses in PACU may rearrange their schedules when they see that patients are being delayed in the operating room.

Indicator (810) indicates surgery delays or late entries into the operating room. Quadrant (802) shows the list of patients in the waiting room. Quadrant (805) shows the list of patients and their status in the PreOp. Quadrant (806) shows the list of patients and their status in the PACU area. For each patient, the user interface (803) shows doctor name, patient initials, type of surgery, time spent by patient at the subject location.

Figure 9:
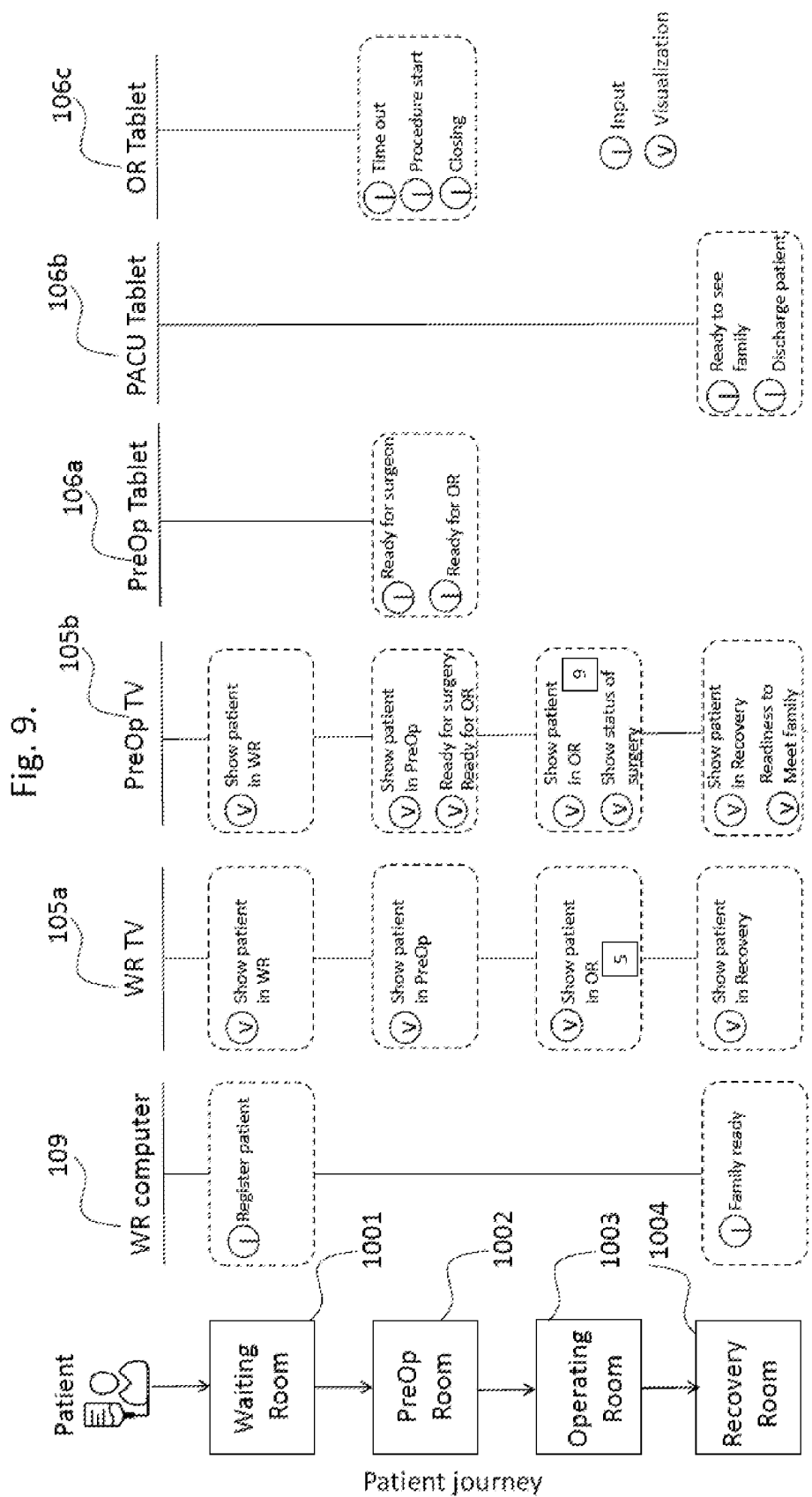
FIG. 9 illustrates a computer interface viewable by front desk personnel according to an embodiment of the present disclosure.

FIG. 9 illustrates computer (109) viewable by front desk personnel. Front desk may have the task to register patients to the system and pair tracking beacon (101) with patient name (902). The list view of patients includes patient name, doctor name, procedure type and patient location. Button (901) allows front desk personnel to signal the readiness of patient's family to meet the patient. When button (901) is selected, label (811) appears on TV screens (105*b*). A beep or a special sound may be simultaneously emitted. Therefore, even when nurses are not looking at the TV screen, they are made aware of a status change. This gives PACU nurses information about family in the waiting room and ready to be accompanied to meet the patient. Button (903) allows front desk assistant to signal the readiness of patients to move to the PreOp.

When button (903) is selected, label (815) appears on TV screens (105b) signaling to the nurse inside the preOp to come and pick up the patient from the waiting room. This optimizes workflow between waiting room staff and preOp staff. Nurses in preOp can just monitor patient status from TV screens (105b) instead of going back and forth to waiting room or calling front desk to ask about patient readiness. The change of status of the patient may also be accompanied by a beep or special sound that nurses may become accustomed to. By hearing this sound, nurses will know that a patient is ready in preOp.

Figure 10:
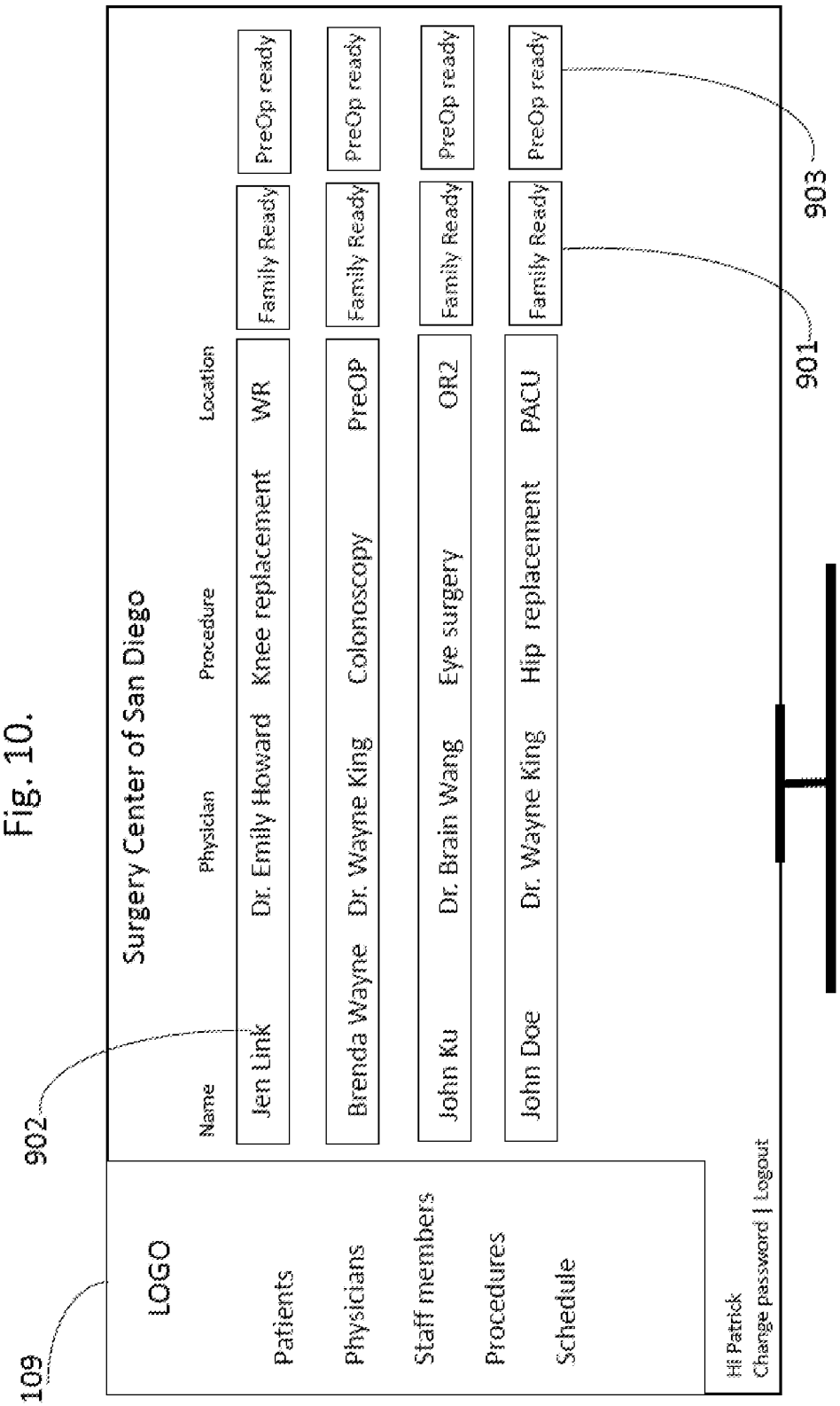
FIG. 10 depicts the types of information input performed by desktop, preOp tablet, PACU tablet and OR tablet according to an embodiment of the present disclosure.

As the patient is tracked from waiting room (1001), to preop room (1002) to operating room (1003) to recovery room (1004), FIG. 10 depicts the types of information input performed by desktop (109), preOp tablet (106a), PACU tablet (106b) and OR tablet (106c). FIG. 10 also illustrates visualization parameters displayed on WR TV (105b), preOp TV (105b).

Input parameters are shown with a circled "I" next to the text in FIG. 9. These include the use of WR computer (109) for patient registration at waiting room (901) and for notifying PACU nurse that the patient family is ready. PreOp tablet (106a) is used to mark patient ready for physician or patient ready for OR. PreOp tablet (106b) is used to mark patient ready to see family or patient discharged. OR tablet (106c) is used to communicate surgery status including Time Out, procedure start, or closing.

Visualization parameters are shown with a circled "V" next to the text in FIG. 9. WR TV (105a) shows patient location and status as patient moves between different rooms of the surgery center. PreOp TV (105b) also visualizes patient location and status as patient moves between different rooms of the surgery center.

While the patient is in PreOp, PreOp TV (105b) visualizes patient readiness to see physician and patient readiness to move to the OR. When the patient moves to the OR, the PreOp TV (105b) shows surgery status for patient. When patient is in PACU, PreOp TV (105b) and PACU TV (105b) visualize patient's readiness to meet family.

Figure 11:
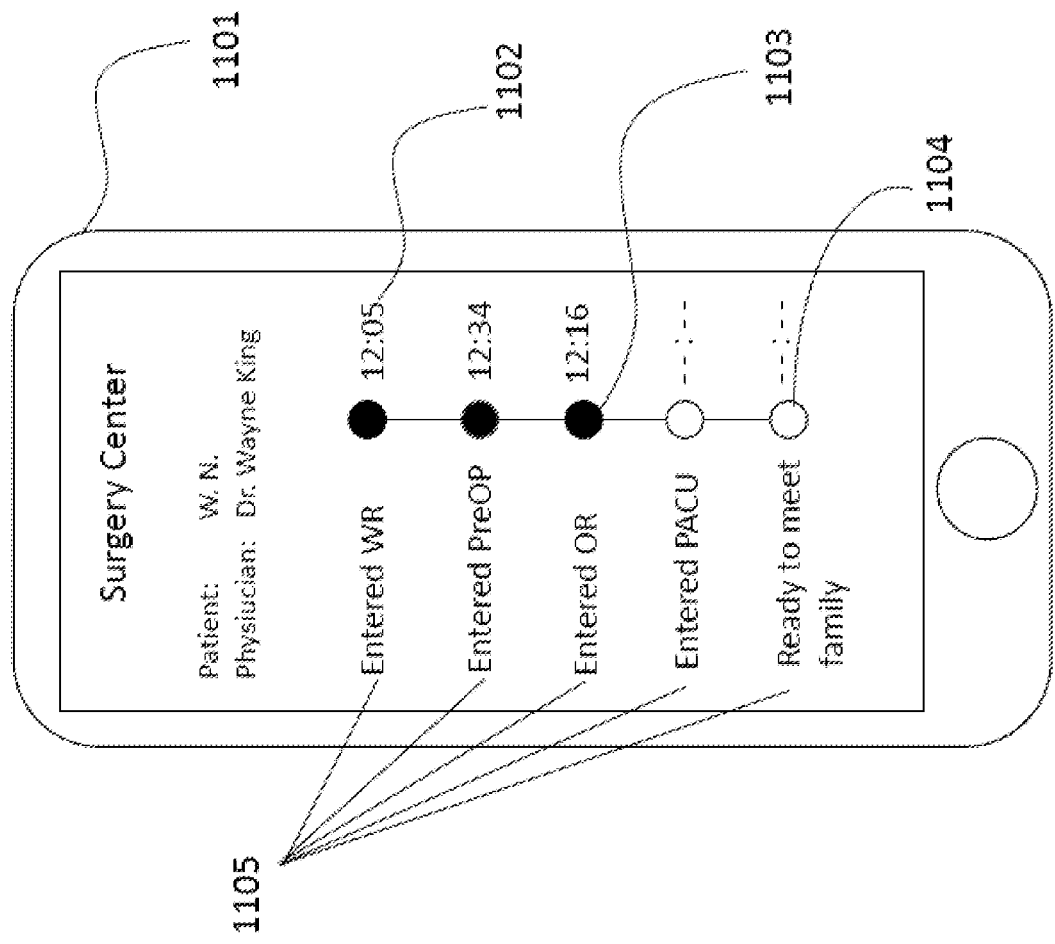
FIG. 11 is an image of a smartphone view of patient status according to an embodiment of the present disclosure.

FIG. 11 shows tracking the patient by a family member from smart phone (1101). As the patient moves between waiting room (301), to preop room (302) to operating room (304a) to recovery room (303), the phone renders patient journey by communicating with application server (108) and displaying patient status (1105) and the time (1102) of status change. Filled dots (1103) show locations visited by the patient while empty dots (1104) are used to show locations yet to be visited by the patient.

What is claimed is:

1. A method for live patient tracking for surgical centers and hospitals, comprising:
   tracking patient journey in terms of location through a healthcare facility in real time;
   overlaying tracked journey data on patient surgical status data; visualizing the overlaid journey data and surgical status data on at least one display;
   wherein the at least one display informs a patient family of the patient journey in terms of patient location and patient status and the at least one display notifies medical staff about events relevant to a workflow in real time for the patient journey.

2. The method according to claim 1, wherein visualization of data is performed on the display of a TV screen, a tablet, a desktop computer, a tablet or a smartphone.

3. The method of claim 1, wherein the visualized data includes patient indoor location within the healthcare facility.

4. The method of claim 3, wherein patient indoor location is performed by means of an indoor positioning system using Real Time Location Service (RTLS) system.

5. The method of claim 1, wherein the visualized surgical status data includes patient readiness to be examined by medical staff or meet loved ones after surgery.

6. The method of claim 5, wherein patient readiness indicates a patient is in preoperative room ready to meet physician or anesthesiologist for preoperative exam.

7. The method of claim 5, wherein patient readiness indicates a patient is in operating room ready to undergo surgery.

8. The method of claim 5, wherein patient readiness indicates a patient is in recovery room (PACU) ready to see loved ones.

9. The method of claim 1, wherein patient journey indicates collection of one or more positions of the patient within a healthcare facility.

10. The method of claim 1, wherein patient surgical status information is entered from a tablet or a smartphone or a desktop computer or a laptop or a touch screen TV.

11. A method for determining patient location within a healthcare facility and patient surgical status at said location, comprising:
    determining that a patient has changed surgical status or said location in real time;
    sending a notification with each change of surgical status or location; and
    overlaying data for said location on data for the surgical status on at least one display;
    wherein the at least one display informs a patient family of the patient journey in terms of patient location and patient status or the at least one display notifies medical staff about events relevant to a workflow in real time for the patient journey.

12. The method of claim 11 wherein the notification is sent via a text message or an email.

13. The method of claim 11, wherein the patient surgical status change indicates a patient is ready to see physician at preoperative room.

14. The method of claim 11, wherein the patient surgical status change indicates a patient is cleared to have surgery.

15. The method of claim 11, wherein the patient surgical status change indicates a patient in recovery room and ready to see loved ones.

16. The method of claim 11, wherein the patient surgical status change indicates a patient in waiting room is ready to move to preoperative room.

17. The method of claim 11, wherein the notification is a special sound made by IV screen, a desktop computer, laptop, a tablet or a smart phone.

18. The method of claim 11, wherein the notification is sent automatically by a cloud server via Bluetooth Low Energy beacon technology used for patient tracking and Bluetooth Low Energy receivers within the healthcare facility, wherein each beacon is uniquely paired with a single patient.

19. The method of claim 11, wherein the notification is triggered manually from a computing device such as a computer, a tablet, or a smartphone.

20. The method of claim 11, wherein the notification is a text message sent to patient's loved ones or medical staff.

21. The method of claim 11, wherein the notification is a text message with a link to a web page that shows live patient journey.

22. The method of claim 11, wherein the notification is a text message for notifying family members that patient entered preoperative or patient entered operating room or patient entered Post-Anesthesia Care Unit or patient woke up and ready to see family members.

* * * * *